United States Patent [19]

Dorn et al.

[11]  4,216,160

[45]  Aug. 5, 1980

[54] SUBSTITUTED MERCAPTO ACID AMIDES AND THEIR USE

[75] Inventors: Conrad P. Dorn, Plainfield; Howard Jones, Holmdel, both of N.J.

[73] Assignee: Merck & Co., Inc., Rahway, N.J.

[21] Appl. No.: 939,293

[22] Filed: Sep. 8, 1978

Related U.S. Application Data

[63] Continuation-in-part of Ser. No. 844,960, Oct. 25, 1977, abandoned.

[51] Int. Cl.² .................. C07C 153/09; C07C 103/32
[52] U.S. Cl. ............................ 260/455 R; 260/561 S; 260/562 S
[58] Field of Search ............. 260/455 R, 561 S, 562 S

[56] References Cited

U.S. PATENT DOCUMENTS

| | | | |
|---|---|---|---|
| 2,456,991 | 12/1948 | Prill | 260/561 S |
| 2,792,307 | 5/1957 | Chenicek | 260/561 S |
| 3,558,640 | 1/1971 | Shen et al. | 546/341 |
| 3,646,138 | 2/1972 | von Strandtmann | 260/558 S |
| 3,671,212 | 6/1972 | Jaworski | 71/77 |

FOREIGN PATENT DOCUMENTS 837847  5/1938  France ................................. 260/455 R

OTHER PUBLICATIONS

Bayles et al., Tetrahedron Letters, No. 51, pp. 4587–4950, (1975).

*Primary Examiner*—Henry R. Jiles
*Assistant Examiner*—Robert C. Whittenbaugh
*Attorney, Agent, or Firm*—Raymond M. Speer; Mario A. Monaco

[57] ABSTRACT

Substituted mercapto acid amides are prepared, and are useful as immunoregulants for correcting an imbalance of immune homeostasis, particularly as immunostimulants in the treatment of autoimmune and immune deficient diseases and disorders.

7 Claims, No Drawings

SUBSTITUTED MERCAPTO ACID AMIDES AND THEIR USE

REFERENCE TO RELATED PRIOR APPLICATIONS

This application is a continuation-in-part of application Ser. No. 844,960, filed Oct. 25, 1977 now abandoned.

DESCRIPTION OF THE INVENTION

The present invention is concerned with novel substituted mercapto acid amides, methods for their preparation, a method of correcting an imbalance of immune homeostasis with the novel compounds, and pharmaceutical compositions containing the novel compounds as active ingredients.

Particularly, the present invention is concerned with novel compounds of structural formula:

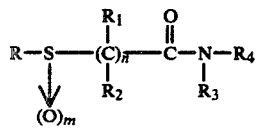

wherein,
m is 0 to 2;
n is 1 to 17;

R is (a) hydrogen; (b) $C_{1-18}$ alkyl, preferably $C_{1-4}$ alkyl, for example, methyl, ethyl, decyl and octadecyl; (c) halo $C_{1-6}$ alkyl, for example, chloromethyl and fluoropropyl; (d) $C_{1-10}$ cycloalkyl, preferably $C_{1-6}$ cycloalkyl, for example, cyclopropyl, cyclohexyl and adamantyl; (e) ar $C_{1-6}$ alkyl, for example, benzyl, substituted benzyl, benzohydryl, triphenylmethyl; (f) $C_{1-4}$ alkoxy $C_{1-6}$ alkyl, for example, ethoxymethyl and methoxyethyl; (g) ar $C_{1-6}$ alkenyl, for example, styryl; (h) aroxy $C_{1-6}$ alkyl, for example, phenoxyethyl; (i) hydroxy $C_{1-6}$ alkyl, for example, hydroxyethyl:

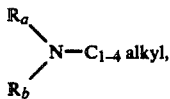

where $R_a$ and $R_b$ are independently selected from hydrogen, $C_{1-4}$ alkyl and phenyl, for example, aminoethyl, methylaminoethyl, diethylaminomethyl, phenylaminomethyl, and diphenylaminoethyl; (k) $C_{1-4}$ alkoxycarbonyl $C_{1-6}$ alkyl, for example, carbomethoxymethyl; (l) $C_{1-4}$ alkylthio $C_{1-6}$ alkyl, for example, methylthiomethyl and propylthioethyl; (m) acyl $C_{1-6}$ alkyl, for example, acetonyl and benzoylmethyl; (n) $C_{1-10}$ alkenyl, for example, vinyl, allyl, and propenyl; (o) $C_{1-6}$ cycloalkenyl, for example, cyclohexenyl; (p) $C_{1-10}$ alkynyl, for example, propargyl; (q) aryl and substituted aryl, for example, phenyl, phenyl substituted with up to 5 radicals independently selected from halo, halomethyl, $C_{1-4}$ alkyl, $C_{1-4}$ alkoxy, sulfide, sulfoxy, sulfonyl, nitro, and cyano; and naphthyl; (r) heterocyclic, and substituted heterocyclic, for example, substituted and unsubstituted radicals of benzimidazole, benzothiazole, benzoxazole, 1,3-dioxane, furan, imidazole, imidazoline, indole, isothiazole, isoxazole, 1,2,4-oxadiazole, 1,3,4-oxadiazole, oxazole, tetrahydropyran, pyrazine, pyrazole, pyrimidine, pyrrole, thiazole, thiophene, triazine, triazole, quinoline, isoquinoline, purine, guanine, pteridine, pyrazolopyrimidine, 4-quinazolinone, and uracil; (s) heterocyclic $C_{1-6}$ alkyl, and substituted heterocyclic $C_{1-6}$ alkyl, for example, substituted and unsubstituted radicals of benzimidazole, benzothiazole, benzoxazole, 1,3-dioxane, 1,3-dioxolane, furan, imidazole, indole, isothiazole, isoxazole, 1,2,4-oxadiazole, oxazole, tetrahydropyran, pyrazine, pyrazole, pyrimidine, thiazole, thiophene, s-triazine, triazole, quinoline, and isoquinoline; (t) acyloxy $C_{1-6}$ alkyl, for example, acetyloxymethyl;

where $R_5$ is (1) $C_{1-18}$ alkyl, for example, methyl, ethyl and octyl; (2) $C_{1-10}$ cycloalkyl, for example, cyclopropyl, cyclohexyl, and adamantyl; (3) ar $C_{1-6}$ alkyl, for example, benzyl; (4) $C_{1-4}$ alkoxy $C_{1-6}$ alkyl, for example, methoxymethyl; (5) aroxy $C_{1-6}$ alkyl, for example, phenoxymethyl; (6) hydroxy $C_{1-6}$ alkyl, for example, hydroxyethyl; (7) acyl $C_{1-6}$ alkyl, for example, acetonyl; (8) $C_{1-4}$ alkoxycarbonyl, for example, carbethoxy and carbomethoxy; (9) $C_{1-4}$ alkoxycarbonyl $C_{1-6}$ alkyl, for example, carbethoxymethyl; (10) acyloxy $C_{1-6}$ alkyl, for example, acetyloxymethyl; (11)

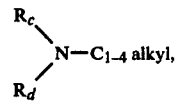

where $R_c$ and $R_d$ are independently selected from hydrogen, $C_{1-4}$ alkyl and phenyl, for example, aminomethyl and diphenylaminoethyl; (12) $C_{1-18}$ alkenyl, for example, vinyl; and undecenyl; (13) $C_{1-10}$ cycloalkenyl, for example, clohexenyl; (14) ar $C_{1-6}$ alkenyl, for example, styryl; (15) $C_{1-10}$ alkynyl, for example, ethynyl; (16) aryl and substituted aryl, for example, phenyl, and phenyl substituted with up to 5 radicals independently selected from halo, halomethyl, $C_{1-4}$ alkyl, $C_{1-4}$ alkoxy, sulfide, sulfoxy, sulfonyl, nitro and cyano; (17) heterocyclic and substituted heterocyclic, for example, substituted and unsubstituted radicals of benzimidazole, benzothiazole, benzoxazole, 1,3-dioxolane, furan, imidazole, indole, isothiazole, isoxazole, oxazole, pyran, tetrahydropyran, pyrazine, pyrazole, pyrimidine, pyrrole, thiazole, thiophene, s-triazine, triazole, quinoline, isoquinoline; (18) heterocyclic $C_{1-6}$ alkyl and substituted heterocyclic $C_{1-6}$ alkyl, for example, substituted and unsubstituted radicals of benzimidazole, benzothiazole, benzoxazole,1,3dioxane, 1,3-dioxolane, furan, imidazole, indole, isothiazole, isoxazole, 1,2,4-oxadiazole, oxazole, tetrahydropyran, pyrazine, pyrazole, pyrimidine, thiazole, thiophene, s-triazine, triazole, quinoline, and isoquinoline; (19) $C_{1-10}$ alkoxy, for example, ethoxy; (20) halo $C_{1-6}$ alkyl, for example, chloromethyl; and

where $R_e$ and $R_f$ are independently selected from hydrogen, $C_{1-4}$ alkyl, and phenyl;

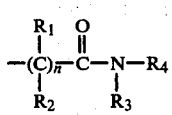

where $R_1$, $R_2$, $R_3$ and $R_4$, and n are as defined herein;

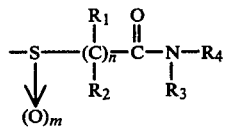

where $R_1$, $R_2$, $R_3$ and $R_4$, and m and n are as defined herein;

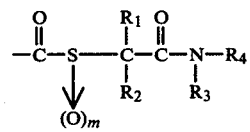

where $R_1$, $R_2$, $R_3$ and $R_4$, and n are as defined herein;

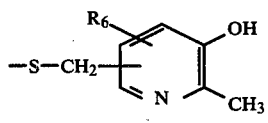

where $R_6$ is 4 or 5: hydroxymethylene, mercaptomethylene, vinyl, or ethynyl;

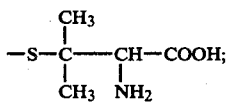

(aa) $SO_3Na$; or (bb) $PO_3Na_2$ $R_1$ and $R_2$ may be the same or different and are independently selected from (a) hydrogen; (b) $C_{1-10}$ alkyl, preferably $C_{1-4}$ alkyl, for example, methyl and ethyl; (c) $C_{1-10}$ cycloalkyl, for example, cyclohexyl; (d) ar $C_{1-6}$ alkyl, and substituted ar $C_{1-6}$ alkyl, for example, benzyl, benzohydryl, triphenylmethyl, and substituted benzyl; (e) $C_{1-4}$ akoxy $C_{1-6}$ alkyl, for example, methoxymethyl; (f) aroxy $C_{1-6}$ alkyl, for example, phenoxypropyl; (g) hydroxy $C_{1-6}$ alkyl, for example, hydroxypropyl;

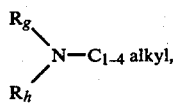

where $R_g$ and $R_h$ are independently selected from hydrogen, $C_{1-4}$ alkyl, and phenyl; (i) $C_{1-4}$ alkylthio $C_{1-6}$ alkyl, for example, ethylthiomethyl; (j) acyl, for example, benzoyl; (k) acyl $C_{1-6}$ alkyl, for example, acetonyl; (l) $C_{1-4}$ alkoxy-carbonyl $C_{1-6}$ alkyl, for example, carbomethoxyethyl; (m) $C_{1-10}$ alkenyl, for example, allyl; (n) $C_{1-10}$ alkynyl, for example, propargyl; (o) aryl and substituted aryl, for example, phenyl, phenyl substituted with up to 5 radicals independently selected from halo, halomethyl, $C_{1-4}$ alkyl, $C_{1-4}$ alkyl, $C_{1-4}$ alkoxy, sulfide, sulfoxy, sulfonyl, nitro, and cyano; (p) heterocylic and substituted heterocyclic for example, substituted and unsubstituted radicals of benzimidazole, benzothiazole, benzoxazole, 1,3-dioxane, furan, imidazole, imidazoline, indole, isothiazole, isoxazole, 1,2,4-oxadiazole, 1,3,4-oxadiazole, oxazole, tetrahydropyran, pyrazine, pyrazole, pyrimidine, pyrrole, thiazole, thiophene, triazine quinoline, isoquinoline, purine, quanine, pteridine, pyrazolopyrimidine, 4-quinazolinone, and uracil; (q) heterocyclic $C_{1-6}$ alkyl, and substituted heterocyclic $C_{1-6}$ alkyl, for example, substituted and unsubstituted radicals of benzimidazole, benzothiazole, benzoxazole, 1,3-dioxane, 1,3-dioxolane, furan, imidazole, indole, isothiazole, isoxazole, 1,2,4-oxadiazole, oxazole, tetrahydropyran, pyrazine, pyrazole, pyrimidine, thiazole, thiophene, s-triazine, triazole, quinoline, and isoquinoline; and (r) halo $C_{1-6}$ alkyl, for example, chloromethyl; and $R_3$ and $R_4$ may be the same or different and are independently selected from (a) hydrogen; (b) $C_{1-18}$ alkyl, preferably $C_{1-4}$ alkyl, for example, methyl and propyl; (c) $C_{1-10}$ cycloalkyl, preferably $C_{1-6}$ cycloalkyl, for example cyclopentyl; (d) ar $C_{1-6}$ alkyl and substituted ar $C_{1-6}$ alkyl, for example, benzyl; (e) $C_{1-4}$ alkoxy $C_{1-6}$ alkyl, for example, methoxy-methyl; (f) aroxy $C_{1-6}$ alkyl, for example, methoxy-methyl; (f) aroxy $C_{1-6}$ alkyl, for example, methoxy-methyl; (g) hydroxy $C_{1-6}$ alkyl, for example, hydroxyethyl;

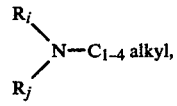

where $R_i$ and $R_j$ are independently selected from hydrogen, $C_{1-4}$ alkyl, and phenyl, for example, dimethylaminomethyl; (i) $C_{1-4}$ alkylthio $C_{1-6}$ alkyl, for example, methylthiopropyl; (j) $C_{1-4}$ alkoxycarbonyl $C_{1-6}$ alkyl, for example, carbethoxymethyl; (k) $C_{1-10}$ alkenyl, for example, propenyl; (l) $C_{1-6}$ cycloalkenyl, for example, cyclohexenyl; (m) $C_{1-6}$ lkynyl, for example, propargyl; (n) aryl and substituted aryl, for example, phenyl, phenyl subsubstited with up to 5 radicals independently selected from halo, halo-methyl, $C_{1-4}$ alkyl, $C_{1-4}$ alkoxy, sulfide, sulfoxy, sulfonyl, nitro and cyano; and naphthyl; (o) heterocyclic and substituted heterocyclic, for example, substituted and unsubstituted radicals of benzimidazole, benzothiazole, benzoxazole, 1,3-dioxane, furna, imidazole, imidazoline, indole, isothiazole, isoxazole, 1,2,4-oxadiazole, 1,3,4-oxadiazole, oxazole, tetrahydropyran, pyrazine, pyrazole, pyrimidine, pyrrole, thiazole, thiophene, triazine, triazole, quinoline, isoquinoline, purine, quanine, pteridine, pyrazolopyrimidine, 4-quinazolinone, and uracil; (p) heterocyclic $C_{1-6}$ alkyl and substituted heterocyclic $C_{1-6}$ alkyl, for example, substituted and unsubstituted radicals of benzimidazole, benzothiazole, benzoxazole, 1,3-dioxane, 1,3-dioxolane, furan, imidazole, indole, isothiazole, isoxazole, 1,2,4-oxadiazoke, oxazole, tetrahydropyran, pyrazine, pyrazole, pyrimidine, thiazole, thiophene, s-triazone, triazole, quinoline, and isoquinoline; (q) halo $C_{1-6}$ alkyl, for example, chloromethyl; and (r)

where $R_5$ is as defined above.

Representative compounds of the present invention are as follows:

N-acetyl-2-(acetylthio)acetamide
N-acetyl-2-(acetylthio)propionamide
N-acetyl-2-(acetylthio)butyramide
N-acetyl-2-(acetylthio-2-phenyl)acetamide
N-acetyl-2-(benzoylthio)acetamide
N-benzoyl-2-(acetylthio)acetamide
N-propionyl-2-(acetylthio)acetamide
N-acetyl-3-(acetylthio)propionamide
N-acetyl-4-(acetylthio)butyramide
N-acetyl-N-methyl-2-(triphenylmethylthio)acetamide
N-acetyl-N-methyl-2-(benzylthio)acetamide
N-acetyl-2-(triphenylmethylthio)acetamide
2-acetylthio acetamide
2,2'-thiobis [N-acetyl acetamide]
N-acetyl-2-mercapto acetamide
2,2' dithiobis [N-acetyl acetamide]
N-acetyl-N-methyl-(2-acetylthio)acetamide
N-acetyl-N-ethyl-2-(acetylthio)acetamide
N-acetyl-2-(ethoxycarbonylthio)acetamide
N-acetyl-2-(diphenylcarbamoylthio)acetamide
N-acetyl-2-(dimethylcarbamoylthio)acetamide
2-acetylthio-N-furoyl acetamide
Sodium N-acetylacetamide-2-S-thiosulfate
N-acetyl-2-(phenylacetylthio)acetamide
S,S'-bis [N-acetyl acetamide-2-yl]carbonodithioate A preferred aspect of the present invention is compounds and the use of active ingredients of structural formula:

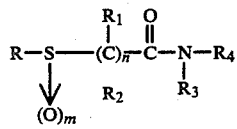

wherein,
n is 1 to 4;
m is 0 to 2;
R is (a) hydrogen; (b) $SO_3Na$; (c) $C_{1-4}$ alkyl; (d) $C_{1-4}$ alkenyl; (e) $C_{1-4}$ alkynyl; (f) phenyl; (g) heterocyclic; (h) $C_{1-6}$ cycloalkyl; (i) ar $C_{1-6}$ alkyl;

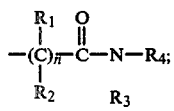 (j)

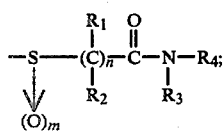 (k)

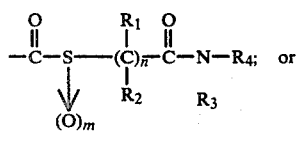 (l)

 (m)

where $R_5$ is (1) $C_{1-18}$ alkyl, (2) $C_{1-10}$ cycloalkyl; (3) ar $C_{1-6}$ alkyl; (4) ar $C_{16}$ alkenyl; (5) $C_{1-4}$ alkoxy $C_{1-6}$ alkyl; (6) $C_{14}$ alkoxycarbonyl $C_{1-6}$ alkyl; (7) $C_{1-18}$ alkenyl; (8) aryl and halo-substituted aryl; (9) heterocyclic and substituted heterocyclic; (10) $C_{1-10}$ alkoxy; and

 (11)

where $R_e$ and $R_f$ are independently selected from hydrogen, $C_{1-4}$ alkyl, and phenyl;

$R_1$ and $R_2$ may be the same or different and are independently selected from
(a) hydrogen; (b) $C_{1-4}$ alkyl; and (c) ar $C_{1-6}$ alkyl; and (d) phenyl; and $R_3$ and $R_4$ may be the same or different and are independently selected from
(a) hydrogen; (b) $C_{1-4}$ alkyl; and

 (c)

where $R_5$ is (1) $C_{1-18}$ alkyl; (2) aryl; (3) ar $C_{1-4}$ alkyl; (4) ar $C_{1-4}$ alkenyl; (5) $C_{1-10}$ cycloalkyl; (6) aroxy $C_{1-4}$ alkyl; (7) heterocyclic and substituted heterocyclic; or (8) $C_{1-4}$ alkoxycarbonyl $C_{1-6}$ alkyl.

Representative of the preferred compounds and active ingredients are the following:
N-acetyl-2-(benzoylthio)acetamide
N-acetyl-3-(acetylthio)propionamide
N-acetyl-N-methyl-2-(triphenylmethylthio)acetamide
N-acetyl-2-(triphenylmethylthio)acetamide
2,2'-thiobis[N-acetyl acetamide]
N-acetyl-2-(ethoxycarbonylthio)acetamide
N-acetyl-2-(diphenylcarbamoylthio)acetamide
N-furoyl-2-(acetylthio)acetamide
Sodium N-acetylacetamido-2-S-thiosulfate
S,S'-bis[N-acetyl acetamid-2-yl]carbonodithioate
N-acetyl-2-benzylsulfinyl acetamide
N-acetyl-2-benzylsulfonyl acetamide
N-acetyl-2-(benzylthio)acetamide
N-acetyl-N-methyl-2-(benzylthio)acetamide
N-acetyl-N-(2-propenyl)-2-(triphenylmethylthio)acetamide
N-acetyl-N-benzyl-2-(triphenylmethylthio)acetamide
N-acetyl-2-phenyl-2-(acetylthio)acetamide
N-acetyl-N-ethyl-2-(acetylthio)acetamide
N-acetyl-2-(2-phenyl-acetylthio)acetamide
N-acetyl-2-(tricyclo[3.3.1.1.$^{3,7}$]decane-1-carbonylthio)acetamide
N-acetyl-2-(2-fluorobenzoylthio)acetamide
N-acetyl-2-(2-methoxy-acetylthio)acetamide
N-acetyl-2-(3,3-dimethylpropanoylthio)acetamide
N-acetyl-2-(hexadecanoylthio)acetamide
N-acetyl-2-[(1-benzopyran-2-one-3-carbonyl)thio]acetamide
N-acetyl-2-(thiophene-2-carbonylthio)acetamide
N-acetyl-2-(1,4-quinoxaline-3-carbonyltho)acetamide
N-acetyl-2-(3-furoylthio)acetamide
N-acetyl-2-(phenothiazine-10-carbonylthio)acetamide
N-acetyl-2-(1-methyl-2-pyrroylthio)acetamide
N-acetyl-2-(quinoline-6-carbonylthio)acetamide
N-acetyl-2-(4,6-dimethyl-pyran-2-one-5-carbonylthio)acetamide
N-acetyl-2-(quinoline-4-carbonylthio)acetamide
N-acetyl-2-(thiazole-4-carbonylthio)acetamide
N-acetyl-2-(2-furoylthio)acetamide
N-acetyl-2-(2-butenoylthio)acetamide N-acetyl-2-(3-phenyl-2-propenoylthio)acetamide
N-acetyl-2-(2-propenoylthio)acetamide
N-acetyl-2-(2-chloro-2,2-diphenyl-acetylthio)acetamide
N-acetyl-2-(butanoylthio)acetamide
N-acetyl-2-(decanoylthio)acetamide
N-acetyl-2-(cyclopropanecarbonylthio)acetamide
N-acetyl-2-(N,N-diethylcarbamoylthio)acetamide
N-acetyl-2-(dodecanoylthio)acetamide
N-acetyl-2-(2-pentenoylthio)acetamide
N-acetyl-2-(octanoylthio)acetamide
N-acetyl-2-(2,2-dimethylpropanoylthio)acetamide
N-acetyl-2-(pentanoylthio)acetamide
N-acetyl-2-(3,3-dimethylbutanoylthio)acetamide
N-acetyl-2-(10-undecenoylthio)acetamide
N-acetyl-2-(N,N-dimethylcarbamoylthio)acetamide
N-(tricyclo[3.3.1.1.$^{3,7}$]decane-1-carbonyl)-2-(acetylthio)acetamide
N-(2-phenylacetyl)-2-(acetylthio)acetamide
N-hexadecanoyl-2-(acetylthio)acetamide
N-(3-phenyl-2-propenoyl)-2-(acetylthio)acetamide
N-(thiophene-2-carbonyl)-2-(acetylthio)acetamide
N-(2-phenoxyacetyl)-2-(acetylthio)acetamide
N-(cyclopropanecarbonyl)-2-(acetylthio)acetamide
N-(3-carbomethoxy-propionyl)-2-(acetylthio)acetamide
N-acetyl-2-triphenylmethyl-2-(benzylthio)acetamide
N-acetyl-2-triphenylmethyl-2-(2-propenylthio)(acetamide
N-acetyl-2-(phenylthio)acetamide
N-acetyl-2-(diphenylmethylthio)acetamide
N-acetyl-2-phenylsulfonyl acetamide
N-acetyl-2-(2-propenylthio)acetamide
N-acetyl-2-(methylthio)acetamide
N-acetyl-2-(benzothiazol-2-ylthio)acetamide
N-acetyl-2-(benzimidazolylthio)acetamide
N-acetyl-2-(2-propynylthio)acetamide
N-acetyl-2-phenylsulfinyl acetamide
N-acetyl-2-(benzoxazol-2-ylthio)acetamide
N-acetyl-2-(pyrid-4-ylthio)acetamide
2,2'-dithiobis[acetamide]
2-(pyrid-2-ylthio)acetamide
2-(benzoxazol-2-ylthio)acetamide
2-(benzothiazol-2-ylthio)acetamide
2-(benzimidazol-2-ylthio)acetamide
2-(methylthio)acetamide
2-(2-propynylthio)acetamide
2-(cyclohexylthio)acetamide
2-(benzoylthio)acetamide A most preferred aspect of the present invention is compounds and the use of active ingredients of structural formula:

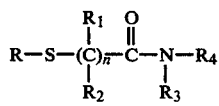

(III)

wherein,
n is 1 to 4;
R is (a) hydrogen;

(b)

where R$_5$ is (1) C$_{1-4}$ alkyl; (2) phenyl; (3) phenyl C$_{1-4}$ alkyl; or (4) C$_{1-4}$ alkoxycarbonyl C$_{1-4}$ alkyl; or

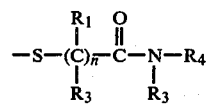

(c)

R$_1$ and R$_2$ may be the same or different and are independently selected from
(a) hydrogen; and (b) C$_{1-4}$ alkyl; and
R$_3$ and R$_4$ may be the same or different and are independently selected from
(a) hydrogen; (b) C$_{1-4}$ alkyl; and

(c)

where R$_5$ is (1) C$_{1-4}$ alkyl; (2) phenyl; (3) phenyl C$_{1-4}$ alkyl; or (4) C$_{1-4}$ alkoxycarbonyl C$_{1-4}$ alkyl; provided that, the above substituents are so selected that at least one carbonyl-containing group is present.

Representative of the most preferred compounds and active ingredients are the following:
N-acetyl-2-(acetylthio)acetamide
N-benzoyl-2-(acetylthio)acetamide
2-(acetylthio)acetamide
N-acetyl-2-mercapto acetamide
2,2'-dithiobis[N-acetyl acetamide]
N-acetyl-N-methyl-2-(acetylthio)acetamide
N-acetyl-2-(phenylacetylthio)acetamide
N-acetyl-N-ethyl-2-(acetylthio)acetamide
N-acetyl-2-(3-carbomethoxy-propionylthio acetamide
N-propionyl-2-(acetylthio)acetamide
N-acetyl-2-methyl-2-(acetylthio)acetamide
N-acetyl-2-(propionylthio)acetamide
N-acetyl-2-(acetylthio)butyramide
2-(phenylacetylthio)acetamide The mercapto or thiol compounds of the present invention may also be utilized in a number of deliverable or latentiatable forms.

It is well known in the art that the mercapto group is subject to reaction with aldehydes and ketones to form hemimercaptals and hemimercattoles. It is similarly known in the art, Field et al., J. Med. Chem. 12, 624-628 (1969) that many of these hemimercaptals and hemimercaptoles prepared from biologically active mercaptans serve as "latentiating" derivatives, or as chemical modifications of biologically active compounds to form new compounds, which upon in vivo enzymatic or chemical transformation will liberate the parent compounds. Latentiation may also provide means of favorably influencing absorption, transport, distribution, localization, metabolism, toxicity, and duration of action, as well as stability. Included with the group of aldehydes and ketones suitable for this purpose are chloral, hexafluoroacetone, acetone, benzaldehyde, pyruvate, and ketomalonate. Since latentiation of mercapto groups by this means is known in the art, these latentiating derivatives are considered to be within the spirit scope of the novel method of treatment and novel compounds of this invention.

Another means of latentiation is by addition of the thiols of this invention to α,β-unsaturated acids such as maleic acid and cinnamic acid as described by Srivistava et al., in J. Med. Chem., 16, 428-429 (1973).

Latentiation may also be achieved by substitution of the mercapto hydrogen with a 1-methyl-4- nitroimidazol-5-yl group as in azathioprine or a pivaloyloxymethyl group.

Presenting, levamisole, (s)-(−)-2,3,5,6-tetrahydro-6-phenylimidazo-[2,1-b]thiazole hydrochloride, is one of the few immunoregulants, or immunepotentiators, in the clinical literature. The clinical efficacy of levamisole in correcting an imbalance of immune homeostasis, and thus its effectiveness in treatment of a number of diseases and disorders characterized or complicated by an imbalance of immune homeostasis, has been confirmed by well-controlled multi-center clinical studies in several diseases and disorders. Consequently, compounds possessing therapeutic properties similar to or better than levamisole would be a valuable contribution to medicine in the field of immunology, and other fields as well. Accordingly, it is an important discovery that the substituted mercapto acid amides of the present invention possess immunological properties similar but superior to those of levamisole, and that they are thus of value in correcting an imbalance of immune homeostasis and for treatment of a number of diseases and disorders characterized or complicated by such an imbalance of immune homeostasis.

Among the diseases and conditions which are characterized or complicated by an imbalance of immune homeostasis are a variety of recurrent and chronic infections and chronic inflammatory conditions. A variety of viral, bacterial, fungal and protozal infections may be subject to treatment. The improvement of the potential of certain vaccines and the prevention of viral immunosuppression may also result. A number of primary immune deficiency or autoimmune diseases may be treated, and allergic disorders such as bronchial asthma may be improved. Various rheumatic diseases, including especially rheumatoid arthritis, may be treated. Certain neurologic disordes and gastrointestinal disorders where an imbalance of immune homeostasis plays a role may be improved by treatment. The treatment of some oncologic diseases may be augmented. Particularly, restoration of immune homeostasis following cytostatic treatment or radiotherapy may be improved.

For use in correcting an imbalance of immune homeostasis and treatment of diseases or disorders characterized or complicated thereby, the compounds of the present invention may be administered orally, topically, parenterally, by inhalation spray or rectally in dosage unit formulations containing conventional nontoxic pharmaceutically acceptable carriers, adjuvants and vehicles. The term parenteral as used herein includes subcutaneous injections, intravenous, intramuscular, intrasternal, intraarticular, injection or infusion techniques. In addition to the treatment of warmblooded animals such as mice, rats, horses, dogs, cats, etc., the compounds of the present invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethyicellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyoxyethylene sorbitan monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxy benzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, ay also be present.

The pharmaceutical compositions of the present invention may also be in the form of oil-in-water emulsions. The oil phase may be a vegetable oil, for example olive oil or arachis oils, or in a mineral oil, for example liquid paraffin or mixtures of these. Suitable emulsifying agents may be naturally-occurring gums, for example gum acacia or gun tragacanth, naturally-occuring phosphatides, for example soya bean lecithin, and esters or partial esters derived from fatty acids and hexitol anhydrides, for example sorbitan monooleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed.

Dosage levels of the order of 0.1 mg. to 140 mg. per kilogram of body weight per day are useful in the treatment of the above-indicated conditions (25 mg. to 7 gms. per patient per day). For example, correction of an imbalance of immunehomeostasis may be accomplished by the administration of about 0.5 to 50 mg. of the compound per kilogram of body weight per day (5 mg. to 3.5 gms. per patient per day). Advantageously, from about 1 mg. to about 15 mg. per kilogram of body weight per daily dosage produces highly effective results (50 mg. to 1 gm. per patient per day).

The amount of active ingredient that may be combined with the carrier materials to produce a single dosage form will vary depending upon the host treated and the particular mode of administration. For example, a formulation intended for the oral administration of humans may contain from 5 mg. to 5 gm. of active agent compounded with an appropriate and convenient amount of carrier material which may vary from about 5 to about 95 percent of the total composition. Dosage unit forms will generally contain between from about 25 mg. to about 500 mg. of active ingredient.

It will be understood, however, that the specific dose level for any particular patient will depend upon a variety of factors including the activity of the specific compound employed, the age, body weight, general health, sex, diet, trime of administration, route of administration, rate of excretion, drug combination and the severity of the particular disease or disorder undergoing therapy.

The compounds of the present invention can be prepared by a number of different methods. A. S-Substituted Compounds 1. The S-substituted compounds of the present invention can be prepared by the S-alkylation or S-acylation of the appropriate thioamide or thioimide according to the following scheme:

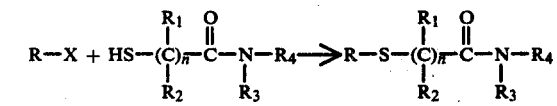

where X is halide or other suitable leaving group and R is as described previously. The reaction can be carried out on the mercaptan itself but is preferably carried out on an alkali metal (Na,K) or heavy metal (Pb, Hg) derivative of the mercaptan. In the case of S-acylation of the mercaptan, a proton acceptor such as triethylamine or pyridine may be used. Representative acid halides which may be used include the following:
Acetyl chloride
O-acetylmandelic acid chloride
O-acetylsalicyloyl chloride
acryloyl chloride
1-adamantane carboxylic acid chloride
p-anisoyl chloride
benzoyl chloride
4-biphenylcarbonyl chloride
t-butylacetyl chloride
butyryl chloride
3-carbomethoxy propionyl chloride
o-chlorobenzoyl chloride
m-chlorobenzoyl chloride
p-chlorobenzoyl chloride
4-chlorobutyryl chloride
α-chloro-α,α-diphenylacetyl chloride
5-chlorovaleryl chloride
cinnamoyl chloride
crotonyl chloride
cyclobutanecarboxylic acid chloride
cyclohexanecarboxylic acid chloride
decanoyl chloride
diethylcarbamoyl chloride
dimethylcarbamoyl chloride
diphenylcarbamoyl chloride ethyl malonyl chloride
ethyl oxalyl chloride
ethyl succinyl chloride
2-furoyl chloride
hexanoyl chloride
isobutyryl chloride
isovaleryl chloride
lauroyl chloride
methacryloyl chloride
methoxyacetyl chloride
myristoyl chloride
nonanoyl chloride 5-norbornene-2-carbonyl chloride
octanoyl chloride
palmitoyl chloride
phenothiazene-10-carbonyl chloride
phenoxyacetyl chloride
phenylacetyl chloride
trans-2-phenylcyclopropane-1-carboxylic acid
propioloyl chloride
2-quinoxaloyl chloride
3,4,5-trimethoxybenzoyl chloride
trimethylacetyl chloride
10-undecenoyl chloride
valeryl chloride
5-fluoro-1-(p-methylthiobenzylidene)-2-methylindenyl-3-acetyl chloride
5-(2,4-difluorophenyl)-salicyloyl chloride The required mercapto amides or mercapto imides may be prepared by the controlled hydrolysis of the corresponding S-acetyl compound and may be isolated as such or as the alkali metal or heavy metal derivatives.

2. In another method, an appropriate mercaptan or thiol acid may be treated with a haloamide or haloimide according to the following scheme:

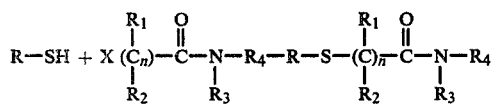

where X is halide or other suitable leaving group.

Again, the free mercaptan may be used but the alkali metal (Na,K) or heavy metal (Hg, Pb) derivative is preferred. Representative mercaptans which may be used include the following:
2-mercaptobenzimidazole
2-mercaptobenzothiazole
2-mercaptobenzoxazole
2-mercapto-4,6-diaminopyrimidine
2-mercapto-4,6-dihyroxypyrimidine
2-mercapto-4,6-dimethylpyrimidine
6-mercaptoguanine
2-mercapto-6-hydroxypurine
2-mercapto-4-hydroxypyrimidine
3-mercapto-5-hydroxy-1,2,4-triazine
2-mercaptoimidazole
8-mercapto-1-methylguanine
6-mercapto-1-methylpurine
2-mercapto-4-methylpyrimidine
6-mercaptonicotinic acid
5-mercapto-1-phenyl-1,2,3,4-tetrazole
2-mercapto-4-phenylthiazole
2-mercaptopteridine
6-mercaptopurine
2-mercaptopyridine
2-mercaptopyridine-N-oxide
4-mercaptopyridine
4-mercapto-1H-pyrazolopyrimidine
2-mercaptopyrimidine
4-mercaptopyrimidine
2-mercapto-4(3H-quinazolinone
2-mercaptoquinoline
4-mercaptoquinoline
2-mercaptothiazoline
3-mercapto-1,2,4-triazole
5-mercaptouracil The haloalkylimides are prepared by the N-acylation of the appropriate haloalkylamides using acyl halides or acid anhydrides according to the procedure of Hurd and Dull [*J. Am. Chem. Soc.* 54, 2435 (1932)].

The haloalkylamides are prepared by treating the corresponding halo acid chloride with concentrated ammonium hydroxide at low temperature (0° C. or less) according to the method of Truitt et al. [*J. Am. Chem. Soc.* 71, 3480 (1949)]. Representative acids which can be converted to the corresponding amides (via the acid chloride) include:
2-chloropropionic acid
2-chlorobutyric acid
α-bromo-cyclopentaneacetic acid
α-bromo-cyclohexaneacetic acid
2-chloro-3-phenylpropionic acid
2-bromo-3,3-diphenylpropionic acid
2-chloro-3-methoxypropionic acid
2-chloro-3-phenoxypropionic acid
2-chloro-4-pentenoic acid
α-chlorophenylacetic acid
α-bromothiophene-3-acetic acid.

The haloalkylamides may also be prepared by treatment of the appropriate haloester with concentrated ammonium hydroxide at low temperature according to the method of Jacobs and Heidelberger [Org. Syn. Coll. Vol. I. 153 (1941)].

Reprsentative haloesters which may be converted to their amides by this procedure include:
methyl 2-chloro-3,3,3-triphenylpropionate
methyl 2-chloro-4-hydroxybutyrate
methyl 2-chloro-4-hydroxybutyrate
methyl 2-chloro-2-methyl-3-methylthiopropionate
ethyl 2-bromolevulinate
2-chloroglutaric acid-5-ethyl ester
methyl α-bromopyridine-2-acetate 3. A method of preparing the S-substituted compounds of the present invention where the substituents are acyl substituents is by reacting N,N-dimethyl-2-mercaptoacet-or higher amidine with an acid halide or anhydride compound in accordance with the following scheme:

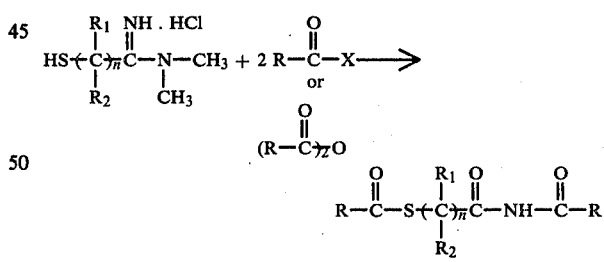

where X is, and is hereinafter defined as, halide or other suitable leaving group.

It will be noted that the above method prepares compounds substituted in an essentially symmetrical fashion, that is, having the same "R" group at either end of the molecule.

B. N-Substituted Compounds

The N-substituted compounds of the present invention may be prepared by several different methods. 1. The N-substituted compounds may be prepared by reacting the appropriate (thio) acid amide or substituted acetamide with a halide compound in accordance with the following scheme:

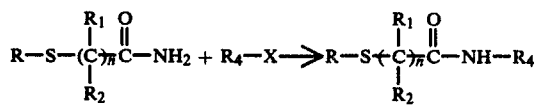

and

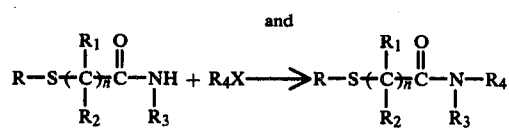

2. Where the R$_4$ substituent is

as defined hereinabove, an acid halide or anhydride compound is employed in accordance with the following scheme:

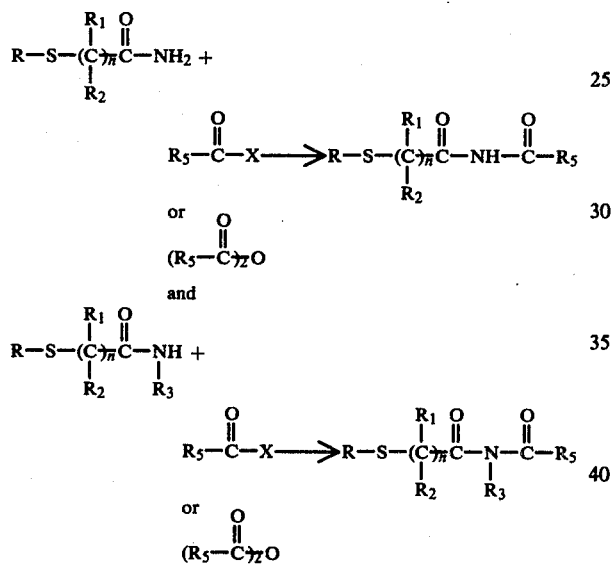

3. The N-substituted compounds of the present invention may also be prepared by reacting the appropriate thioacid halid with an amine or amide compound in accordance with the following scheme:

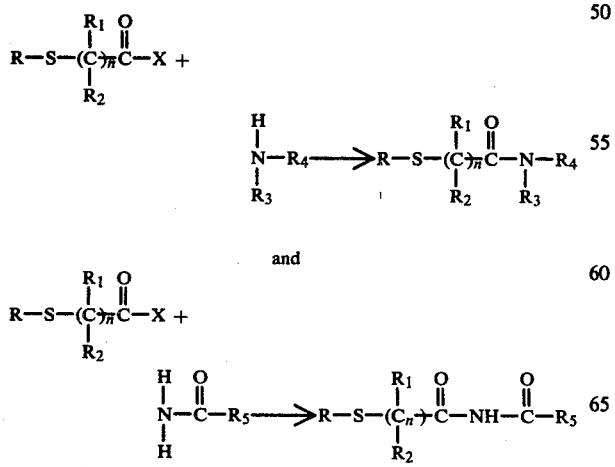

4. In a method similar to that set out in A.3. above, N,N-dimethyl-2-substituted-mercapto-acet-or higher amidine may be reacted with an acid halide or anhydride compound in accordance with the following scheme:

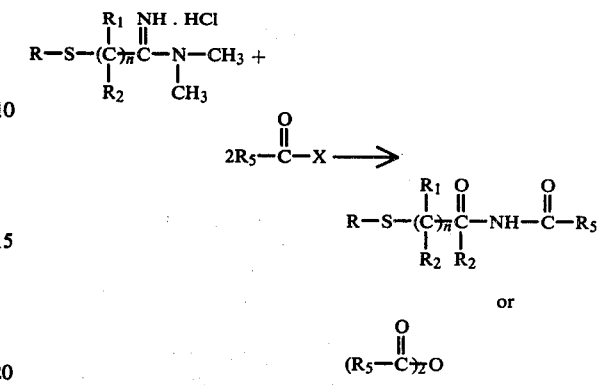

5. Another method, in addition to those shown above, for providing the tertiary amine compounds of the present invention, that is, where for $$-\underset{R_3}{\underset{|}{N}}-R_4,$$

both R$_3$ and R$_4$ are other than hydrogen, is that where the appropriate (thio) acid amide is reacted with sodium hydride and then a halide compound in accordance with the following scheme:

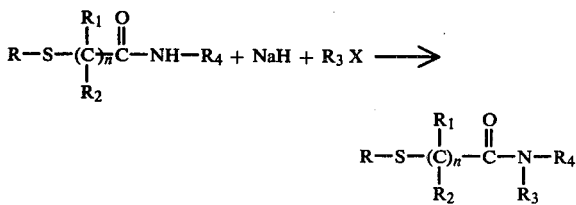

C. Higher Acid Amides

Higher acid amide compounds of the present invention, for example, propionamide and butyramide compounds, may be prepared by reacting the appropriate halo acid amide with a thio acid, preferably in its alkali metal salt form, in accordance with the following scheme:

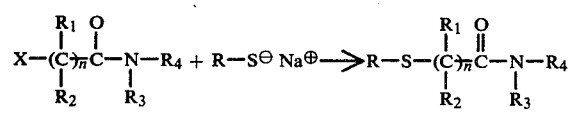

where n=2 to 17.

The halo acid amide, in turn, may be prepared from the corresponding cyanide by graded hydrolysis, as for example with cold concentrated hydrochloric acid, in accordance with the following scheme:

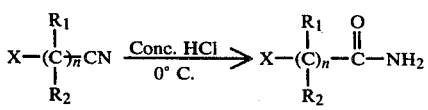

The amine group may be substituted, in turn, by means of the method described in B.1. above.

D. Sulfur Oxidation

The sulfur oxidation analogs of the (thio) acid amide compounds, that is, sulfinyl and sulfonyl acid amides of the present invention, may be prepared by oxidation of the corresponding thio acid amide using an appropriate oxidation agent such as an alkali metal salt of periodic acid or hydrogen peroxide to product the sulfinyl and sulfonyl compounds, respectively, in accordance with the following scheme:

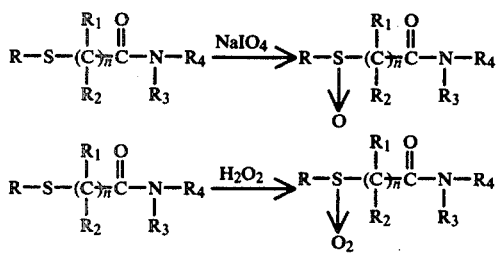

Various other synthetic procedures are employed to prepare mercapto acid amides with the desired substitution possessed by the compounds of the present invention.

The examples which follow illustrate preparation of specific novel compounds of the present invention from known starting materials.

EXAMPLE 1

N-acetyl-2-(acetylthio) acetamide

To a solution of 0.1 mole of sodium hydroxide in 300 ml. of anhydrous methanol through which nitrogen has been bubbled for 5 minutes is added 0.11 mole of thiolacetic acid. The resulting solution is stirred for 5 minutes and there is then added 0.1 mole of N-acetyl-2-chloroacetamide. After the initial exothermic reaction subsides the mixture is refluxed for 5 minutes, cooled and concentrated to dryness. The residue is slurried with 75 mls. of water and filtered. Recrystallization from water yields N-acetyl-2-(acetylthio)acetamide (10.0 g.) (m.p. 140°–142° C.).

Employing the procedure described above, but substituting for the thiolacetic acid an equivalent amount of thiopropionic acid, there is produced N-acetyl-2-propionylthio acetamide.

Employing the procedure described above, but substituting for the N-acetyl-2-chloroacetamide an equivalent amount of N-acetyl-2-chloropropionamide; N-acetyl-2-chlorobutyramide; and N-acetyl-2-chloro-2-phenyl acetamide; there is produced, respectively, N-acetyl-2-(acetylthio)propionamide; N-acetyl-2-(acetylthio)-butyramide; and N-acetyl-2-(acetylthio-2-phenyl)acetamide.

EXAMPLE 2

N-acetyl-2-(benzoylthio)acetamide

To a solution of 0.05 mole of sodium hydroxide in 40 ml. of water through which nitrogen has been bubbled for 5 minutes and which has been cooled to 0°–5° C., is added 0.052 mole of thiolbenzoic acid. The resulting yellow solution is stirred for 2 minutes and then 0.05 mole of N-acetyl-2-chloro-acetamide is added. The resulting mixture is heated on the steam bath for 10 minutes than cooled to 0°–5° C. and filtered. The product is washed with cold water and air dried. Recystallization from ethanol gives 7.0 g. of N-acetyl-2-(benzoylthio)-acetamide (m.p. 115°–116° C.).

EXAMPLE 3

N-Benzoyl-2-(acetylthio)acetamide

To a solution of 0.02 mole of sodium hydroxide in 50 ml. of methanol which has been cooled to 0°–5° C. and through which a stream of nitrogen has been bubbled for 5 minutes is added 0.021 mole of thiolacetic acid. The resulting solution is stirred for 5 minutes and then 0.021 mole of N-benzoyl-2-chloroacetamide is added. After stirring at ambient temperature for 1 hour the reaction mixture is heated to reflux for 5 minutes, then cooled and concentrated to dryness. The residue is slurried with water (50 ml), filtered and air dried. Recrystallization from ethanol gives 4.35 g. of N-benzoyl-2-(acetylthio)acetamide.

Employing the procedure described above, but substituting for the N-benzoyl-2-chloroacetamide an equivalent amount of N-propionyl-2-chloroacetamide, there is produced N-propionyl-2-(acetylthio)acetamide.

EXAMPLE 4

N-acetyl-3-(acetylthio) propionamide

Step A: Preparation of N-acetyl-3-chloropropionamide

A mixture of 0.2 mole 3-chloropropionamide, 35 ml. of acetic anhydride and 1 ml. acetylchloride is refluxed under nitrogen for 1 hour and then concentrated in vacuo to give crude N-acetyl-3-chloropropionamide as an oil which is used in the next step without purification.

Step B: Preparation of Nacety-3-(acetylthio) propionamide

To a solution (0°–5° C.) of 0.3 mole of sodium hydroxide in 250 ml. of methanol through which nitrogen has been bubbled for 15 minutes is added 0.3 mole of thiolacetic acid. The solution is stirred for 5 minutes and there is then added a solution of N-acetyl-3-chloropropionamide (from Step A above) in 100 ml. of methanol. The reaction mixture is refluxed for 2 hours, cooled, filtered and the filtrate concentrated in vacuo. Chromatography of the residue on 500 g. of silica gel eluting with ethyl acetate in methylene chloride (2.5 to 10%) gives 5.71 g. of N-acetyl-3-(acetylthio)propionamide (m.p. 103.5°–104.5° C.).

Employing the procedure described above, but substituting for the 3-chloropropionamide an equivalent amount of 4-chlorobutyramide, there is produced N-acetyl-(4-acetylthio) butyramide.

EXAMPLE 5

N-acetyl-N-methyl-2-(triphenylmethylthio) acetamide

To a solution of 0.01 mole of N-acetyl-2-(triphenylmethylthio) acetamide in 25 ml. of dimethylformamide which has been cooled to 0°–5° C. is added 0.01 mole of sodium hydride (5% suspension in mineral oil). After the evolution of hydrogen ceases 0.015 mole of methyl iodide is added and the reaction mixture is allowed to stir at room temperature overnight. The reaction mixture is then poured into a mixture of 200 ml. benzene and 250 ml. of water containing 5 g. of ammonium chloride. The organic layer is separated, washed well with water, dried over sodium sulfate, and concentrated in vacuo. Chromatography of the residue on 300 g. of silica gel, eluting with 50% ether in hexane gives 2.6 g.

of N-acetyl-N-methyl-2-(triphenylmethylthio) acetamide.

Employing the procedure described above, but substituting for the N-acetyl-2-(triphenylmethylthio) acetamide an equivalent amount of N-acetyl-2-benzylthio acetamide, there is provided N-acetyl-N-methyl-2-(benzylthio) acetamide.

EXAMPLE 6

N-acetyl-2-(triphenylmethylthio) acetamide

A mixture of 0.009 mole of triphenylmethyl mercaptan and 0.009 mole of triethylamine in 10 ml. of dimethylformamide is cooled to 0°–5° C. in an ice bath and 0.009 mole of N-acetyl-2-chloroacetamide added. The reaction mixture is stirred at ambient temperature for three hours and then poured into 100 ml. of benzene and 100 ml. of water. The organic layer is separated, washed well with water, dried over sodium sulfate and concentrated to dryness. The residue is crystallized under petroleum ether to give 2.2 g. of Nacetyl-2-(triphenylmethylthio) acetamide.

EXAMPLE 7

2-(acetylthio)acetamide

To a solution of 0.1 mole sodium hydroxide in 200 ml. of methanol at 0°–5° C. and under nitrogen is added 0.1 mole of thiolacetic acid. After 5 minutes 0.1 mole of 2-chloroacetamide is added and the reaction mixture is refluxed for 1 hour and then concentrated in vacuo. The residue is extracted with 100 ml. of boiling isopropanol, filtered, and the filtrate concentrated in vacuo. The residue is recrystallized from toluene to give 11.39 g. of 2-(acetylthio)acetamide.

EXAMPLE 8

2,2'-thiobis[N-acetyl acetamide]

A solution of 0.05 mole of potassium hydroxide in 100 ml. of absolute ethanol is saturated with hydrogen sulfide and then 0.05 mole of N-acetyl-2-chloro acetamide and 100 ml. of ethanol is added. The reaction mixture is stirred at ambient temperature for 1½ hours during which time a slow stream of hydrogen sulfide is bubbled through. The reaction mixture is then stripped in vacuo. The residue is extracted with 150 ml. of boiling ethyl acetate and filtered. The precipitate is washed 3 times with 50 ml. of water, air dried and then recrystallized from acetic acid to give 6.09 g. of 2,2'-thiobis[N-acetyl acetamide] (m.p. 98°–101° C.).

EXAMPLE 9

N-acetyl-2-mercapto acetamide

To a suspension of 0.06 mole of N-acetyl-2-acetythioacetamide in 150 ml. of methanol, under nitrogen, and cooled to 0°–5° C. is added dropwise a solution of 0.06 mole of sodium hydroxide in 40 ml. of methanol. The reaction mixture is stirred cold for ½ hour after the addition is complete, acidified with acetic acid and concentrated to dryness. The residue is stirred with 40 ml. of water at 0°–5° C. under nitrogen and filtered. The precipitate is recrystallized from ethanol to give 4.12 g. of N-acetyl-2-mcercapto acetamide.

EXAMPLE 10

2,2'-Dithiobis[N-acetylacetamide]

A suspension of 0.06 mole of N-acetyl-2-(acetylthio) acetamide in 40 ml. of methanol is cooled to 0°–5° C. and a solution of 0.06 mole of sodium hydroxide in 30 ml. of methanol is added dropwise. The reaction mixture is stirred cold for ½ hour, acidified with acetic acid, and 10 ml. of 30% hydrogen peroxide is added dropwise. The reaction mixture is stirred overnight at room temperature and then concentrated to dryness. The residue is stirred with 25 ml. of cold water and filtered to give 2.85 g. of 2,2'-dithiobis[N-acetylacetamide].

EXAMPLE 11

N-acetyl-N-methyl-2-acetylthio acetamide

To a solution of 0.06 mole of N-acetyl-2-(acetylthio) acetamide in 50 ml. of dimethylformamide which has been cooled to 30° C. is added portionwise 0.06 mole of sodium hydroxide. After stirring the reaction mixture at 30° C. to 40° C. until the evolution of hydrogen ceases, 0.0652 mole of methyl iodide is added. The reaction mixture is allowed to warm to room temperature and is stirred for ½ hour. There is then added 100 ml. of ether, 30 ml. of 2.5N HCl, and 70 ml. of water. The aqueous layer is separated and extracted three times with 100 ml. of ether. The combined ether extracts are washed well with water, dried over sodium sulfate, and concentrated in vacuo. The residue is chromatographed on 800 g. of silica gel and eluted with 25% ether in hexane to give 2.8 g. of N-acetyl-N-methyl-2-(acetylthio) acetamide.

Employing the procedure described above, but substituting for the methyl iodide an equivalent amount of ethyl iodide, there is produced N-acetyl-N-ethyl-2-(acetylthio) acetamide.

EXAMPLE 12

N-acetyl-2-(ethoxycarbonylthio) acetamide

To a suspension of 0.06 mole of N-acetyl-2-(acetylthio) acetamide in 100 ml. of methanol under nitrogen and cooled to 0°–5° C. is added a solution of 0.06 mole of sodium hydroxide in 25 ml. of methanol. The reaction mixture is stirred at 0° C. for 2 hours and then concentrated in vacuo. The residue is treated with 25 ml. of 2.5 N hydrochloric acid and concentrated to dryness to yield crude N-acetyl-2-mercapto acetamide. The above material is suspended in 100 ml. of chloroform and 0.09 mole of ethyl chlorocarbonate is added, followed by 10 ml. of triethyl amine. The reaction mixture is stirred at ambient temperature for ½ hour and then concentrated to dryness. The residue is treated with 25 ml. of water and 5 ml. of 2.5 N hydrochloric acid. The product is filtered and recrystallized two times from water to give 3.0 g. of N-acetyl-2-(ethoxycarbonylthio)acetamide.

EXAMPLE 13

N-acetyl-2-(diphenylcarbamoylthio) acetamide

To a suspension of 0.05 mole of N-acetyl-2-(acetylthio) acetamide in 100 ml. of methanol cooled to 0°–5° C. under nitrogen is added a solution of 0.05 mole of sodium hydroxide in 50 ml. of methanol. The reaction mixture is stirred cold for 1 hour and then concentrated to dryness. The residue is suspended in 100 ml. of dimethylformamide and 0.05 mole of diphenyl-carbamoyl chloride is added. The reaction mixture is stirred at ambient temperature for 2 hours, concentrated in vacuo, and the residue taken up between ethylacetate and dilute hydrochloric acid. The organic layer is separated, washed well with water, and dried over sodium sulfate and concentrated. Chromatography of the residue on 600 g. of silica gel eluting with ethylacetate in hexane (25–50%) gives 1.8 g. N-acetyl-2-(diphenylcarbamoylthio) acetamide.

Employing the procedure described above, but substituting for the diphenylcarbamoyl chloride an equivalent amount od dimethylcarbamoyl chloride, there is produced N-acetyl-2-(dimethylcarbamoylthio) acetamide.

EXAMPLE 14

2-acetylthio-N-furoyl acetamide

A mixture of 0.01 mole of 2-acetylthio acetamide and 5 ml. of furoyl chloride is heated on the steam bath for 3 hours and then concentrated in vacuo. Chromatography of the residue on 250 g. of silica gel eluting with 25% ethyl acetate in hexane gives 0.12 g. of 2-acetylthio-N-furoyl acetamide.

EXAMPLE 15

Sodium N-acetylacetamido-2-S-thiosulfate

A mixture of 0.01 mole of N-acetyl-2-chloro acetamide and 0.01 mole of sodium thiosulfate 5 H$_2$O in 15 ml. of water is heated on the steam bath for ½ hour and then concentrated in vacuo. Recrystallization of the residue from a small amount of water give sodium N-acetyl acetamide-2-S-thiosulfate.

When trisodium phosphorothioate is used in place of sodium thiosulfate in the above procedure there is obtained disodium N-acetylacetamido-2-S-thiophosphate.

EXAMPLE 16

N-Acetyl-2-(phenylacetylthio) acetamide

To 0.10 mole of N-acetyl-2-mercapto acetamide in 150 ml. of chloroform is added 0.1 mole of phenyl acetylchloride followed by 0.1 mole of triethylamine. The reaction mixture is stirred at ambient temperature for 1 hour and then concentrated to dryness. Chromatograph of the residue on 500 g. of silica gel eluting with ethylacetate in hexane (25–75%) gives N-acetyl-2-(phenylacetylthio) acetamide.

EXAMPLE 17

S,S'-bis [N-acetyl acetamide-2-yl] carbonodithioate

To 0.1 mole of N-acetyl-2-mercapto acetamide in 250 ml. of chloroform which has been cooled to 0° to 5° C. is added 0.05 mole of phosgene (12.5% in benzene) followed by 0.1 mole of pyridine. The reaction mixture is stirred overnight at ambient temperature and then concentrated to dryness. Chromatography of the residue on 500 g. of silica gel eluting with ethylacetate in hexane (25–80%) gives S,S'-bis [N-acetyl acetamide-2-yl] carbonodithioate.

EXAMPLE 18

N-Acetyl-2-benzylsulfinylacetomide

To a solution of 0.011 mole of NaIO$_4$ in 25 ml. of water which has been cooled to 5° C. is added 0.01 mole of N-acetyl-2-(benzylthio) acetamide. The reaction mixture is allowed to warm to room temperature and then stirred overnight and concentrated to dryness. Chromatography of the residue on 200 g. of silica gel eluting with ethyl acetate in hexane (25–75%) gives N-acetyl-2-benzylsulfinylacetamide.

EXAMPLE 19

N-Acetyl-2-benzylsulfonylacetamide

To a stirred solution of 0.01 mole of N-acetyl-2-(benzylthio)acetamide in 50 ml. of acetic acid is added 2 ml. of 20% hydrogen peroxide. The reaction mixture is heated on the steam bath for 1 hour and then concentrated in vacuo. Treatment of the residue with water gives crude product which is recrystallized from methanol to give N-Acetyl-2-benzylsulfonyl-acetamide.

EXAMPLE 20

N-acetyl-2-phenyl-2-(acetylthio)acetamide

A. 2-chloro-2-phenyl acetamide

To 150 ml. of concentrated ammonium hydroxide and 75 g. of ice was added 20 g. of 2-chloro-2-phenylacetylchloride. The amide formed immediately. The reaction mixture was stirred for 30 minutes and the white solid precipitate which was collected weighed 16.9 g. This precipitate was dissolved in 100 ml. of hot ethyl acetate and then diluted with petroleum ether, after which there was collected 14.3 g. of white cottony needles having an m.p. of 120°–121° C.

B. N-acetyl-2-chloro-2-phenylacetamide

To a solution of one drop of concentrated sulfuric acid in 5 ml. of acetic anhydride was added 2 g. of the amide of Step A above, and the reaction mixture was heated on a steam bath for 1.5 hours. The resulting yellow solution was stirred with ice and water and 2.1 g. of precipitate was soon collected. The precipitate was dissolved in about 15 ml. of dichloromethane, after which petroleum ether was carefully added to near the cloud point. Short white needles of precipitate formed to give a yield of 1.9 g. having an m.p. of 101°–102° C.

C. N-acetyl-2-phenyl-2-(acetylthio)acetamide

The triethylamine salt of thiolacetic acid was made by adding 2.23 g. (0.022 mole) of triethylamine to a stirred and ice-cooled solution of 1.67 g. (0.022 mole) of thiolacetic acid in 15 ml. of dimethylformamide. This solution was in turn added dropwise with stirring and ice-cooling to a solution of 4.2 g. (0.02 mole) of the compound prepared in Step B. above in 15 ml. of dimethylformamide, while maintaining the temperature below 10° C. The reaction mixture was stirred an additional hour, and then there was added 1 ml. of acetic acid. The reaction mixture was poured onto ice and a thick yellow oil formed. The mixture was decanted, and the ice was washed with water and again decanted. The yellow oil was taken up in 75 ml. of ether, dried, and evaporated, leaving 2.5 g. of yellow oil. This was chromatographed on a Waters high pressure liquid chromatography apparatus using 25% ethylacetate in hexane as the eluent. A water-white oil weighing 1.9 g. was obtained. A seed was formed by rubbing a little with petroleum ether and the bulk of material precipitated quickly to yield 1.6 g. of material having an m.p. of 96° C.

EXAMPLE 21

N-acetyl-2-ethyl-2-(acetylthio)acetamide

A. 2-chlorobutyramide

To 20 g. of 2-chlorobutyric acid there was added 30 ml. of sulfonyl chloride. After the initial reaction subsided, the solution was heated to gentle reflux on a steam bath for 3 hours. The solution was concentrated to about one-half volume by blowing nitrogen through the warm solution, after which it was added dropwise to 100 ml. of ammonium hydroxide and about 50 g. of ice. The amide formed quickly as a white solid. The reaction mixture was stirred for 30 minutes, after which the product was collected and then washed once with ice-water. The product was taken up in 100 ml. of warm chloroform and a small amount of insoluble material was removed. The filtrate was evaporated giving 12.9 g. of amide having an m.p. 75°–77° C.

B. N-acetyl-2-chlorobutyramide

A solution of 25 ml. of acetic anhydride containing 2 drops of concentrated sulfuric acid and 5 g. of the amide prepared in Step A. above was heated on a steam bath for 3 hours. The reaction mixture as evaporated in vacuo and the yellow oily residue was taken up in 75 ml. of dichloromethane, which was in turn extracted twice with 50 ml. of water, dried, and evaporated to yield 5.2 g. of product. A small amount was recrystallized from petroleum ether, giving small white crystals having an m.p. of 51°–53° C.

C. N-acetyl-2-ethyl-2-(acetylthio) acetamide

To a cooled solution of 3.36 g. (0.044 mole) of thiolacetic acid in 30 ml. of dry dimethylformamide was added, over 5 minutes, 4.46 g. (0.044 mole) of triethylamine. This cooled solution was then added dropwise with stirring over 20 minutes to a solution of 6.52 g. (0.04 mole) of the amide prepared in Step B. above in 40 ml. of dry dimethylformamide. The temperature of the reaction mixture was kept below 10° C. while it was stirred an additional hour, after which it was allowed to stand at room temperature overnight. The reaction mixture was then evaporated in high vacuum at about 40° C. and the resulting residue was extracted between 200 ml. of ether and 25 ml. of water. The ether layer was dried and evaporated leaving 6.1 g. of oil which was chromatographed on a Waters high pressure liquid chromatography apparatus with 5% ethylacetate in dichloromethane, giving 5.1 g. of product. The oil crystallized on standing and had an m.p. of 59°–60° C.

EXAMPLE 22

N-acetyl-2-(2-phenyl-acetylthio) acetamide

A. N-acetyl-2-mercapto acetamide

Nitrogen was bubbled through a suspension of 8.75 g. (0.05 mole) of N-acetyl-2-(acetylthio) acetamide prepared in accordance with the procedures of Example 1 above in 100 ml. of methanol at $-5°$ C. for 10 minutes. Then there was added, over 15 minutes, a solution of 2 g. (0.05 mole) of sodium hydroxide in 20 ml. of methanol at $-5°$ C. The reaction mixture was stirred an additional hour at $-5°$ C. with nitrogen being bubbled through constantly. There was then added 3 g. (0.05 mole) of acetic acid and the reaction mixture was evaporated in vacuo, after which 50 ml. of ice-water was added and a complete solution obtained.

B. N-acetyl-2-(2-phenyl-acetylthio) acetamide

One-half of the aqueous solution prepared in Step A. above was taken and ice was added while nitrogen was bubbled through the stirred solution. There was then added 4.65 g. (0.03 mole) of phenylacetyl chloride, and after that, with good stirring, there was added over 20 minutes a solution of 1.2 g. (0.03 mole) of sodium hydroxide in 30 ml. of water. Ice was added in intervals while the reaction mixture was stirred an additional hour. The water was then decanted from the solid product, after which it was triturated with cold water and decanted, then triturated with 0.5 ml. of acetic acid in 50 ml. of cold water and decanted. The solid was taken up in dichloromethane, dried, then evaporated to an oil. The oil was triturated with petroleum ether, after which it solidified, yielding 3.2 g. The product was recrystallized from dichloromethane/petroleum ether to yield 2.0 g. This material was chromatographed on a Waters high pressure liquid chromatography apparatus using silica gel and hexane: ethylacetate (2:1) as the eluent. A total of 800 mg. of product was obtained having an m.p. of 123°–124° C.

EXAMPLE 23

N-acetyl-2-(3-carbomethoxy-propionylthio) acetamide

A. N-acetyl-2-mercapto acetamide

A slurry of 8.75 g. (0.05 mole) of N-acetyl-2-(acetylthio) acetamide in 100 ml. of methanol at $-5°$ C. was formed and nitrogen was bubbled through the slurry. Then 2.0 g. (0.05 mole) sodium hydroxide was added and the reaction mixture was aged for 1 hour. Next, 3.0 g. (0.05 mole) acetic acid (2.9 ml.) was added and the reaction mixture was concentrated under vacuum at low temperature.

B. N-acetyl-2-(3-carbomethoxy-propionylthio) acetamide

The concentrated product of Step A. above was added to 100 ml. of dichloromethane and cooled to $-5°$ C. under nitrogen. There was then added 8.3 g. (0.055 mole) of 3-carbomethoxypropionyl chloride in 20 ml. of dichloromethane, over from 5 to 10 minutes. Next, there was added 5.57 g. (0.055 mole) of triethylamine in 20 ml. of dichloromethance and the reaction mixture was aged for 1 hour at $-5°$ C., then permitted to come to room temperature over 2 hours. The reaction mixture was then concentrated under vacuum after having been made slightly acidic with acetic acid. Ice water was then added to the reaction mixture, and the water was extracted with dichloromethane dried over magnesium sulfate and concentrated to an oil of 15.4 g. The oil was changed to a silica gel column and eluted with 25% ethylacetate/hexane to obtain 2.3 g. of final product having an m.p. of 111°–113° C.

EXAMPLES 24–56

In the following Examples the procedures of Example 23 above were followed to first obtain N-acetyl-2-mercapto acetamide from N-acetyl-2-(acetylthio) acetamide, and then there was substituted for the 3-carbomethoxypropionyl chloride of Example 23, equimolar amounts of the carbonyl chloides set out in the following table, which also identifies the products obtained and their melting points where applicable.

| EXAMPLE NO. | CARBONYL CHLORIDE | WEIGHT (g.) | FINAL PRODUCT | WEIGHT (g.) | MELTING POINT (°C.) |
|---|---|---|---|---|---|
| 24 | CH$_3$CH=CHCOCl | 5.8 | N-acetyl-2-(2-butenoylthio) acetamide | 2.3 | 120.5–122 |

-continued

| EXAMPLE NO. | CARBONYL CHLORIDE | WEIGHT (g.) | FINAL PRODUCT | WEIGHT (g.) | MELTING POINT (°C.) |
|---|---|---|---|---|---|
| 25 | PhCH=CHCOCl | 9.2 | N-acetyl-2-(3-phenyl-2-propenoylthio)acetamide | 7.7 | 162–164 |
| 26 | $CH_2$=CHCOCl | 4.98 | N-acetyl-2-(2-propenoylthio)acetamide | 0.35 | 115–116.5 |
| 27 | $Ph_2$C(Cl)COCl | 14.6 | N-acetyl-2-(2-chloro-2,2-diphenyl-acetylthio)acetamide | 5.6 | 114.5–116 |
| 28 | $CH_3CH_2CH_2COCl$ | 4.16 | N-acetyl-2-(butanoylthio)acetamide | 1.2 | 98.5–100.5 |
| 29 | $CH_3(CH_2)_8COCl$ | 7.44 | N-acetyl-2-(decanoylthio)acetamide | 2.0 | 93–94 |
| 30 | cyclopropyl-COCl | 4.08 | N-acetyl-2-(cyclopropanecarbonylthio)acetamide | 1.1 | 131–132 |
| 31 | $(CH_3CH_2)_2$NCOCl | 5.29 | N-acetyl-2-(N,N-diethyl-carbamoylthio)acetamide | 2.3 | oil |
| 32 | 4-phenylbenzoyl chloride | 6.5 | N-acetyl-2-(4-phenylbenzoylthio)acetamide | 0.8 | 177–179 |
| 33 | $CH_3(CH_2)_{10}COCl$ | 8.53 | N-acetyl-2-(dodecanoylthio)acetamide | 5.4 | 92–94 |
| 34 | $(CH_3)_2$C=CHCOCl | 4.62 | N-acetyl-2-(2-pentenoylthio)acetamide | 2.4 | 84–85 |
| 35 | $CH_3(CH_2)_6COCl$ | 6.34 | N-acetyl-2-(octanoylthio)acetamide | 2.3 | 91–92 |
| 36 | $(CH_3)_3$C-COCl | 4.70 | N-acetyl-2-(2,2-dimethyl-propanoylthio)acetamide | 3.0 | oil |
| 37 | $CH_3(CH_2)_3COCl$ | 4.70 | N-acetyl-2-(pentanoylthio)acetamide | 1.7 | 77–79 |
| 38 | $(CH_3)_3$C-$CH_2$COCl | 5.25 | N-acetyl-2-(3,3-dimethyl-butanoylthio)acetamide | 1.3 | 66–68 |
| 39 | $CH_2$=CH-$(CH_2)_8$-COCl | 7.91 | N-acetyl-2-(10-undecenoylthio)acetamide | 1.7 | 77.5–79 |
| 40 | cyclobutyl-COCl | 4.62 | N-acetyl-2-(cyclobutanecarbonylthio)acetamide | 0.77 | 73–75 |
| 41 | cyclohexyl-COCl | 5.72 | N-acetyl-2-(cyclohexanecarbonylthio)acetamide | 1.9 | 84–86 |
| 42 | adamantyl-COCl | 3.4 | N-acetyl-2-(tricyclo[3.3.1.1.3,7]decane-1-carbonylthio)acetamide | 1.9 | 103–105 |
| 43 | 2-fluorobenzoyl chloride | 5.4 | N-acetyl-2-(2-fluoro-benzoylthio)acetamide | 1.4 | 105–107 |
| 44 | $CH_3O$-$CH_2$-COCl | 4.3 | N-acetyl-2-(2-methoxy- | 1.8 | 95–96 |

-continued

| EXAMPLE NO. | CARBONYL CHLORIDE | WEIGHT (g.) | FINAL PRODUCT | WEIGHT (g.) | MELTING POINT (°C.) |
|---|---|---|---|---|---|
| | | | acetylthio)acetamide | | |
| 45 | (CH₃)₂CH—CH₂—COCl | 4.8 | N-acetyl-2-(3,3-dimethyl-propanoylthio)acetamide | 2.3 | 58–60 |
| 46 | CH₃(CH₂)₁₄COCl | 10.0 | N-acetyl-2-(hexadecanoyl-thio)acetamide | | 102–103 |
| 47 | coumarin-3-COCl [1] | | N-acetyl-2-[(1-benzopyran-2-one-3-carbonyl)thio]acetamide | 0.55 | 222–223 |
| 48 | thiophene-2-COCl | 4.4 | N-acetyl-2-(thiophene-2-carbonylthio)acetamide | 1.65 | 119–120 |
| 49 | quinoxaline-3-COCl | 5.0 | N-acetyl-2-(1,4-quinoxaline-3-carbonylthio)acetamide | 0.90 | 177–179 |
| 50 | 3-furoyl-COCl [2] | | N-acetyl-2-(3-furoyl-thio)acetamide | 1.6 | 115–116 |
| 51 | phenothiazine-10-COCl | 6.83 | N-acetyl-2-(pheno-thiazine-10-carbonyl-thio)acetamide | 3.7 | 167–171 |
| 52 | 1-methyl-pyrrole-2-COCl [3] | | N-acetyl-2-(1-methyl-2-pyrroylthio)acetamide | 1.6 | 75–76 |
| 53 | quinoline-6-COCl [4] | | N-acetyl-2-(quinoline-6-carbonylthio)acetamide | 0.90 | 143–144 |
| 54 | 4,6-dimethyl-pyran-2-one-5-COCl [5] | | N-acetyl-2-(4,6-dimethyl-pyran-2-one-5-carbonyl-thio)acetamide | 3.3 | 168–170 |

[1] The acid chloride was prepared from 5.7 g. (0.03 mole) of coumarin-3-carboxylic acid in 50 ml. of sulfonyl chloride which was refluxed for 1 hour and then evaporated to give a crystalline solid which was used without purification.
[2] The 3-furoyl chloride was prepared by refluxing 15 g. of the corresponding acid in 40 g. of sulfonyl chloride for 2 hours and then evaporating. The crude oily product was used without further purification.
[3] The acid chloride was prepared by refluxing 15 g. of the corresponding acid in 30 ml. of sulfonyl chloride for 1.5 hours, then pulling off the excess sulfonyl chloride and using the crude acid chloride, a very dark oil, without further purification.
[4] The acid chloride was prepared from 10.4 g. (0.06 mole) of quinoline-6-carboxylic acid and 30 g. of sulfonyl chloride which were refluxed together for 2 hours, then evaporated in vacuo.
[5] The acid chloride was prepared from 10.1 g. (0.06 mole) of the corresponding acid and 50 g. of sulfonyl chloride which were refluxed together for 2 hours and then evaporated to a crystalline solid.
[6] The acid chloride was prepared from 10.4 g. (0.06 mole) of quinoline-4-carboxylic acid and 35 g. of sulfonyl chloride, which were refluxed for 2 hours and then evaporated to yield a yellow solid which was extracted with ether.
[7] The acid chloride was prepared by refluxing 5 g. (0.039 mole) of thiazole-4-carboxylic acid in 35 ml. of sulfonyl chloride for 2.5 hours and then evaporating in vacuo to form a crystalline material.

EXAMPLE 57

N-acetyl-N-ethyl-2-(acetylthio)acetamide

A solution of 11 g. (0.063 mole) of N-acetyl-2-(acetylthio)acetamide in 75 ml. of dry dimethylformamide was cooled to −30° C. and there was then added 3.02 g. (0.063 mole) of 50% sodium hydride. The reaction mixture was aged until hydrogen evolution ceased. There was then added 5.1 ml. (0.063 mole) of ethyl iodide after cooling the reaction mixture to −40° C., after which the reaction mixture was allowed to come to room temperature and age overnight. A precipitate formed. There was next added 5 ml. of acetic acid, then 100 ml. of ether, followed by 30 ml. of 2.5 N hydrochloric acid and 70 ml. of water. The ether layer was separated and the water layer was increased to about 400 ml. with water, after which it was extracted three times with 100 ml. of ether. The ether extract was dried over magnesium sulfate and concentrated to an oil of 7.2 g. Composition of the product was verified by NMR and mass spectrometry.

EXAMPLE 58

N-acetyl-2-triphenylmethyl-2-(2-propenylthio)acetamide

Step A: Preparation of N-acetyl-2-chloroacetamide

To a mixture of 186 g. of 2-chloroacetamide and 250 ml. of acetic anhydride was added 10 ml. of concentrated sulfuric acid, and the reaction mixture was heated on a steam bath in a nitrogen atmosphere for 1.5 hours. The reaction mixture was then cooled and ether was added until it was near the cloud point. The product formed as a voluminous solid. A total of 500 ml. of ether was added and the reaction mixture was stirred overnight, after which the product was collected and washed several times with ether. The yield was 249 g. with an m.p. of 104°–107° C.

Step B: Preparation of N-acetyl-2-(triphenylmethylthio)acetamide

To a suspension of 100.4 g. (0.40 mole) of triphenylmethylmercaptan in 500 ml. of dry dimethylformamide was added 40.4 g. (0.40 mole) of dry triethylamine. The reaction mixture was cooled in ice and stirred as portions of 54.2 g. (0.40 mole) of the product of Step A above were added over 10 minutes. The reaction mixture was stirred an additional hour with ice cooling and then overnight at room temperature. Water was then added carefully to the reaction mixture until just before the cloud point, when the mixture was seeded and crystallization began. Yield of product was 98.5 g. with an m.p. of 147°–149° C.

Step C: Preparation of N-acetyl-2-triphenylmethyl-2-(2-propenylthio)acetamide

To 3.75 g. (0.01 mole) of the product of Step B above in 100 ml. of acetone was added 672 mg. (0.012 mole) of powdered potassium hydroxide, and the reaction mixture was stirred at room temperature for 15 minutes. There was then added 1.2 g. (0.01 mole) of allyl bromide. The reaction mixture became cloudy and was stirred overnight at room temperature, after which some solid was found to be present. The reaction mixture was evaporated in vacuo and ice-water was added to the residue, after which it was decanted and taken up in 50 ml. of boiling ethanol. A yield of 600 mg. of light tan needles was obtained, m.p. 193°–194° C.

EXAMPLE 59

N-acetyl-2-triphenylmethyl-2-(benzylthio)acetamide

To 3.75 g. (0.01 mole) of the product of Example 58, Step B above, in 30 ml. of dry dimethylformamide was added 288 mg. (0.012 mole) of sodium hydride. The reaction mixture was stirred for 20 minutes and there was then added 1.5 g. (0.012 mole) of benzyl chloride, followed by stirring at room temperature overnight. The cloudy reaction mixture was then poured into ice water, and the resulting solid was filtered off and then chromatographed on a Waters high pressure liquid chromatography apparatus, using 20% ethylacetate in hexane as the eluent. A yield of 1.9 g. was obtained, m.p. 184°–186° C.

EXAMPLE 60

N-acetyl-2-(2-furoylthio)acetamide

Step A: Preparation of 2-(2-furoylthio)acetamide

A slurry was prepared from 8.75 g. (0.05 mole) of N-acetyl-2-(acetylthio)acetamide and 100 ml. of methanol at −5° C., and nitrogen was bubbled through the slurry. There was then added 2.0 g. (0.05 mole) of sodium hydroxide in 20 ml. of methanol. The reaction mixture was aged for 1 hour and then concentrated under high vacuum while the temperature was kept below 30° C. Next, 100 ml. of dimethylformamide was added and the reaction mixture was cooled to 0° C. There was then added 7.2 g. (0.055 mole) of 2-furoyl chloride, and the reaction mixture was aged for 3 hours at 0° C., after which it was concentrated under high vacuum. The residue was charged to a silica gel column and eluted with 50% ethylacetate/hexane. The product was recrystallized from toluene and air dried to yield 2.9 g., m.p. 126°–128° C.

Step B: Preparation of N-acetyl-2-(2-furoylthio)acetamide

A reaction mixture comprising 2.8 g. of the product of Step A above, 30 ml. of acetic anhydride and 2 ml. of acetyl chloride, was heated on a steambath for 6 hours. The reaction mixture was then cooled and poured into ice water, giving a gummy solid after about 15 minutes. The product was filtered and air dried to yield 1.1 g. This was recrystallized from toluene to yield 0.65 g., m.p. 103°–105° C.

EXAMPLE 61

N-acetyl-2-(N,N-dimethylcarbamoylthio)acetamide

Step A. Preparation of N-acetyl-2-mercapto acetamide

A suspension of 8.75 g. (0.05 mole) of N-acetyl-2-(acetylthio)acetamide in 100 ml. of methanol was cooled to −5° C. and nitrogen was bubbled through for 10 minutes. There was then added a solution of 2.0 g. (0.05 mole) of sodium hydroxide in 20 ml. of methanol. THe reaction mixture was stirred for 1 hour at −5° C. and then 5 ml. of concentrated hydrochloric acid was added. The reaction mixture was stripped under vacuum until a dry product remained.

Step B: Preparation of N-acetyl-2-(N,N-dimethylcarbamoylthio)acetamide

The product of Step A above was suspended in 100 ml. of dichloromethane and cooled to −5° C., after which 6.0 g. (0.055 mole) of N,N-dimethylcarbamoyl chloride in 20 ml. of dichloromethane was added. There was then added dropwise a solution of 9 ml. of triethylamine in 25 ml. of dichloromethane, while the temperature of the reaction mixture was kept below 0° C. The reaction mixture was then aged overnight at room temperature, and then stripped in vacuo and pumped dry. The reaction mixture was then stirred with 50 ml. of water, cooled in an ice bath, filtered, and washed with 25 ml. of cold water. A yield of 6.02 g. of tan fluffy crystals was obtained.

EXAMPLE 62

N-(2-phenylacetyl)-2-(acetylthio)acetamide

A reaction mixture comprising 6.65 g. (0.05 mole) of 2-(acetylthio)acetamide, 10 ml. of 2-phenylacetyl chloride, and 1 drop of sulfuric acid was heated in a steam bath for 0.5 hour, and then allowed to stand overnight at room temperature, after which it solidified. There was then added 50 ml. of ether and 20 ml. of hexane, followed by stirring for 10 minutes and then filtering. A yield of 8.5 g. of a tan solid was obtained, which was then chromatographed on 100 g. of silica gel, eluting with 5% ether in dichloromethane, followed by concentration to dryness. The solid was suspended in 60 ml. of ethanol and stirred in an ice bath for 1 hour. The product of white crystals, m.p. 153°–155° C., was obtained in a 5.6 g. yield.

EXAMPLES 63–67

Following the procedures of Example 62 above, but substituting for the 2-phenylacetyl chloride of that Example, equimolar amounts of the carbonyl chlorides set out in the following table, there were obtained the various N-substituted-2-(acetylthio)acetamides indicated in the table, together with their melting points, where applicable.

The organic layer was separated and the aqueous layer was extracted once with 100 ml. of chloroform. The combined organic layers were washed with water, dried over sodium sulfate, and concentrated to give 13.5 g. of dark brown oil. The oil was chromatographed on 1 kg. of silica gel, eluting with 50% ether/hexane, to give 0.75 g. of final product.

EXAMPLE 69

N-acetyl-2-(acetylthio)acetamide

To a solution of 1.55 g. (0.01 mole) of N,N-dimethyl-2-(acetylthio)acetamidine hydrochloride in 25 ml. of dichloromethane was added 8.4 ml. (0.06 mole) of triethylamine, followed by 3.8 ml. (0.04 mole) of acetic anhydride, after which the reaction mixture was allowed to stand overnight at room temperature. The reaction mixture was concentrated in vacuo, after which it was chromatographed on 200 g. of silica gel, eluting with methanol/dichloromethane (1%/10%). The main product was isolated and recrystallized from ethanol and then ethylacetate/hexane. Structure of the

| EXAMPLE NO. | CARBONYL CHLORIDE | AMOUNT | FINAL PRODUCT | WEIGHT (g.) | MELTING POINT (°C.) |
|---|---|---|---|---|---|
| 63 | $CH_3(CH_2)_{14}COCl$ | 8 ml. (0.045 mole) | N-hexadecanoyl-2-(acetylthio)acetamide | 1.02 | 122.5–124.5 |
| 64 | C₆H₅—CH=CH—COCl | 7.5 g. | N-(3-phenyl-2-propenyl)-2-(acetylthio)acetamide | 1.51 | 156–157 |
| 65 | C₆H₅—O—CH₂—COCl | 6.2 ml. (0.045 mole) | N-(2-phenoxyacetyl)-2-(acetylthio)acetamide | 0.47 | — |
| 66 | cyclopropyl—COCl | 4.1 ml. (0.045 mole) | N-(cyclopropanecarbonyl)-2-(acetylthio)acetamide | 5.0 | — |
| 67 | $CH_3O-\overset{O}{\underset{\|}{C}}-(CH_2)-COCl$ | 5.6 ml. (0.045 mole) | N-(3-carbomethoxypropionyl)-2-(acetylthio)acetamide | 0.98 | |

EXAMPLE 68

N-(thiophene-2-carbonyl)-2-(acetylthio)acetamide

Step A: Preparation of N,N-dimethyl-2-(acetylthio)acetamidine hydrochloride

To a solution of 1.54 g. of N,N-dimethyl-2-(mercapto)acetamidine hydrochloride in 15 ml. of acetic acid was added 2 ml. of acetic anhydride, and the reaction mixture was heated at 55°–60° C. for 3 hours, after which it was concentrated in vacuo. The product was crystallized from ether, filtered, and air dried, then recrystallized from ethanol to yield 1.1 g., m.p. 162°–5-°–163° C.

Step B: Preparation of N-(thiophene-2-carbonyl)-2-acetylthio)acetamide

A reaction mixture comprising 9.8 g. of N,N-dimethyl-2-(acetylthio)acetamidine hydrochloride and 7.0 ml. of thiophene-2-carbonyl chloride in 200 ml. of dichloromethane, under a nitrogen blanket, was cooled to −30° to −48° C. in dry ice/acetone. There was then added 25 ml. of triethylamine in 50 ml. of dichloromethane, and the reaction mixture was allowed to warm to room temperature, where it was kept for 2 hours. The reaction mixture was concentrated in vacuo and the residue was extracted between 300 ml. of dichloromethane, 100 ml. of 2.5 N hydrochloric acid, and 100 ml. of water.

product was confirmed by NMR.

EXAMPLE 70

N-propionyl-2-(acetylthio)acetamide

Nitrogen was bubbled through 4.0 g. (0.1 mole) of sodium hydroxide in 200 ml. of methanol and to this there was added 7.1 ml. (0.1 mole) of thioacetic acid and then 16.0 g. (0.1 mole) of N-propionyl-2-chloroacetamide. The reaction mixture was stirred at ambient temperature for 2 hours and then stripped in vacuo and filtered. The product was dissolved in boiling water, treated with charcoal, filtered and dried in vacuo. A yield of 6.0 g. of white crystalline product was obtained.

EXAMPLE 71

N-methyl-N-acetyl-2-(benzylthio)acetamide

Step A: Preparation of N-acetyl-2-(benzylthio)acetamide

To a solution of 1.75 g. (0.01 mole) of N-acetyl-2-(acetylthio)acetamide in 20 ml. of dimethylformamide was added 0.5 g. of 50% sodium hydride. After evolution of hydrogen stopped, there was added 1.5 ml. of benzyl chloride and the reaction mixture was heated on a steam bath for 4 hours. The product was chromatographed by thin layer chromatography eluting with 40% ethylacetate/hexane, then 15 g. of silica gel was added and the product was stripped in vacuo. The prepack was chromatographed on 200 g. of silica gel, eluting with 15% ethylacetate/hexane. A yield of 0.65 g. of product was recrystallized from isopropanol, m.p. 86°–87° C.

Step B: Preparation of N-methyl-N-acetyl-2-(benzylthio)acetamide

A solution of 11.15 g. (0.05 mole) of the product of Step A above in 75 ml. of dimethylformamide was cooled to −5° C. and there was then added 2.4 g. (0.05 mole) of 50% sodium hydride. The reaction mixture was aged for 30 minutes at −5° C., after which there was added 3.2 ml. (0.05 mole) of methyl iodide, and the reaction mixture was aged for 1 hour, 15 minutes at 0° C. and 45 minutes at room temperature. The reaction mixture was poured into ice water, seeded and placed in a refrigerator overnight. It was then filtered, washed with water and air dried. A yield of 9.0 g. of product was obtained.

EXAMPLE 72

N-acetyl-2-methyl-2-(acetylthio)acetamide

To a solution of 0.64 g. of sodium hydroxide (0.016 mole) in 50 ml. of methanol through which nitrogen had been bubbled for 15 minutes was added 1.5 ml. of thiacetic acid and the reaction mixture was aged for 15 minutes. There was then added 2.4 g. (0.016 mole) of N-acetyl-2-methyl-chloroacetamide in 30 ml. of methanol. The reaction mixture was refluxed under nitrogen for 2 hours, after which it was filtered and concentrated in vacuo to an oil of 3.9 g. The oil was charged to a silica gel column and eluted with 20% ethylacetate/hexane, and the product was concentrated to 1.8 g. of white solid, m.p. 91°–93° C.

EXAMPLE 73

N-acetyl-2-(propionylthio)acetamide

To a solution of 4.0 g. (0.1 mole) of sodium hydroxide in 50 ml. of water, cooled in ice and having nitrogen bubbled therethrough, was added 9.5 g. (0.1 mole) of thiopropionic acid. The reaction mixture was stirred for 5 minutes, after which there was added 13.7 g. of N-acetyl-chloroacetamide in 50 ml. of water. The reaction mixture was heated on a steam bath for 10 minutes, then cooled, filtered, and air dried. The product was washed with ether/hexane (3:1) three tims with 150 ml. each washing, and then air dried. The product was recrystallized from water to yield 8.0 g. of white crystals.

EXAMPLE 74

N-acetyl-2-(acetylthio)butyramide

Step A: Preparation of 4-chlorobutyramide

To 500 ml. of concentrated hydrochloric acid at 0° C. was added 81 g. (0.78 mole) of 4-chlorobutyronitrile, and the reaction mixture was aged overnight at room temperature. The reaction mixture was then concentrated under vacuum, azeotraped with benzene, and pumped dry overnight, after which it was extracted with hot toluene and the solid product was allowed to crystallize.

Step B: Preparation of N-acetyl-2-(acetylthio)butyramide

To a solution of 1.04 g. (0.26 mole) of sodium hydroxide in 25 ml. of methanol through which nitrogen had been bubbled for 15 minutes was added 1.98 g. (0.26 mole) of thioacetic acid, and the resulting yellow solution was aged for 10 minutes. To this solution was then added 3.65 g. (0.022 mole) of the product of Step A above in 30 ml. of methanol, and the reaction mixture was refluxed under nitrogen for 6 hrs., after which it was cooled, filtered, and concentrated under vacuum to an oil of 5.26 g. The oil was chromatographed on 250 g. of silica gel, eluting with ether/hexane (1:1), and the final product concentrated to 1.8 g., m.p. 77°–79° C.

What is claimed is:

1. A compound of structural formula:

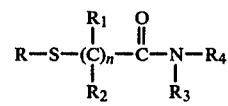

n is 1 to 4;
R is (a) hydrogen;

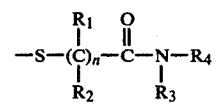 (b)

where
R$_5$ is
(1) C$_{1-4}$ alkyl;
(2) C$_{1-4}$ alkoxy C$_{1-4}$ alkyl;
(3) C$_{3-6}$ cycloalkyl;
(4) phenyl;
(5) phenyl C$_{1-4}$ alkyl; or
(6) C$_{1-4}$ alkoxycarbonyl C$_{1-4}$ alkyl;

 (c)

R$_1$ and R$_2$ may be the same or different and are independently selected from
(a) hydrogen; and
(b) C$_{1-4}$ alkyl; and
R$_3$ and R$_4$ may be the same or different and are independently selected from
(a) hydrogen;
(b) C$_{1-4}$ alkyl; and

 (c)

where
R$_5$ is
(1) C$_{1-4}$ alkyl;
(2) C$_{1-4}$ alkoxy C$_{1-4}$ alkyl;
(3) C$_{3-6}$ cycloalkyl;
(4) phenyl;
(5) phenyl C$_{1-4}$ alkyl; or
(6) C$_{1-4}$ alkoxycarbonyl C$_{1-4}$ alkyl;
provided that, with regard to all of the above substituents, at least one carbonyl-containing group is selected.

2. A compound of claim 1 which is N-Acetyl-2-(acetylthio)acetamide.

3. A compound of claim 1 which is N-Acetyl-N-methyl-2-(acetylthio)acetamide.

4. A compound of claim 1 which is N-benzoyl-2-(acetylthio)acetamide.

5. A compound of claim 1 which is N-propionyl-2-(acetylthio)acetamide.

6. A compound of claim 1 which is N-acetyl-2-(propionylthio)acetamide.

7. A compound of claim 1 which is N-acetyl-3-(acetylthio)propionamide.

* * * * *